United States Patent [19]

Ziegelmeyer

[11] Patent Number: 4,636,220
[45] Date of Patent: Jan. 13, 1987

[54] ADJUSTABLE PROSTHETIC FOOT

[75] Inventor: Harold R. Ziegelmeyer, Medford, Oreg.

[73] Assignee: John W. Campbell, Medford, Oreg.

[21] Appl. No.: 818,768

[22] Filed: Jan. 14, 1986

[51] Int. Cl.4 .............................................. A61F 2/66
[52] U.S. Cl. ..................................................... 623/53
[58] Field of Search ........................ 623/47, 53, 54, 55

[56] References Cited

U.S. PATENT DOCUMENTS

| 4,089,072 | 5/1978 | Glabiszewski | 623/53 |
| 4,302,856 | 12/1981 | May | 623/55 |
| 4,328,594 | 5/1982 | Campbell et al. | 623/55 |
| 4,413,360 | 11/1983 | Lamb et al. | 623/53 |

FOREIGN PATENT DOCUMENTS 2080115 2/1982 United Kingdom .................. 623/53

Primary Examiner—Richard J. Apley
Assistant Examiner—James Prizant
Attorney, Agent, or Firm—Neil J. Driscoll

[57] ABSTRACT

An arrangement for adjusting the heel height of a prosthetic foot includes a cavity at the rear aspect of the prosthetic foot adapted to receive a separate locking block therein. Both the locking block and the cavity, as seen inside elevational view, are arcuate in configuration. Secured to the lower aspect of the block are a pair of arcuate rails spaced transversely from each other. Secured to the upper surface of the cavity and in complementary relation to the arcuate rails are a pair of transversely spaced grooves or tracks to receive the respective rails. The locking block may be moved longitudinally and arcuately of the prosthetic foot to thereby adjust the heel height of the foot when it is secured to a prosthetic device. A locking bolt is used to accomplish the attachment of the foot to the device and hold the block in fixed position to maintain the desired heel height.

4 Claims, 7 Drawing Figures

ADJUSTABLE PROSTHETIC FOOT

BACKGROUND OF THE INVENTION

1. Field of the Invention

The present invention relates to a prosthetic foot, and, more particularly to a foot wherein the heel height thereof may be adjusted.

2. Description of the Prior Art

Amputees have utilized prosthetic feet since the adoption of the wooden peg leg of pirate fame during the seventeenth century and earlier. A brief history of prior art prosthetic feet is described and set out in U.S. Pat. No. 4,328,594, issued May 11, 1982, and entitled Prosthetic Foot by named inventors John W. Campbell and Charles W. Childs. Both of Medford, Oreg. The entire disclosure of U.S. Pat. No. 4,328,594 is expressly incorporated herein by reference, hence, the details thereof will not be redundantly repeated herein. Suffice it to say that the prosthetic foot advance detailed in U.S. Pat. No. 4,328,594 provided the art a foot capable of dorsiflexion, plantarflexion, and foot inversion and eversion. The net affect is that the foot disclosed and described in the referenced U.S. Patent closely mimics the movement of the human foot.

There is however, a need extant in the prosthetic foot art which would allow the user of such a foot to adjust the heel height in a positive way and when the need arises, e.g., when changing from one pair of shoes to another. It is also necessary that the adjusted heel height be permanent during use and not loosen thereby affecting the gait of wearer.

SUMMARY OF THE INVENTION

The herein disclosed invention is shown as applied to a prosthetic foot comprising an elongated semi-rigid keel incorporating a raised, half dome shaped arch. A thinned toe break region extends laterally across the forward aspect of the keel. The keel has a cavity which receives a bolt block which, with the keel, forms a keel-bolt block assembly. The keel-bolt block assembly includes arcuate precision machined rails which are secured to the undersurface of the removable bolt block. Matching arcuate precision machined grooves or tracks are securely connected to the keel and define a lower segment of the bolt block cavity formed within the keel of the prosthetic foot. The rails as seen in transverse section, are wedge shaped and are congruently received in the grooves or tracks secured to the keel. Apertures are provided in both the rail member and the groove member which receives a threaded bolt which extends upwardly through openings in the prosthetic foot and the bolt block for threadably securing the foot to a prosthetic device worn by the amputee. The bolt, therefore, secures the bolt block rigidly to the keel of the foot. It will be understood, the bolt block may be rotated longitudinally of the long axis of the foot to vary the position of the upper surface of the bolt block inrelation of the long axis of the prosthetic device worn by the amputee. The result is the heel height of the prosthetic foot may be varied to any level desired by the wearer.

Accordingly, it is a primary objection of the invention to provide a prosthetic foot of the type described with a mode of readily adjusting the heel height of the foot as required by the needs of the wearer.

It is a further object of the invention to provide a mechanical mode for assuredly locking the bolt block assembly to the keel of the prosthetic foot so that the desired heel height will be maintained during use.

The above and other objects and advantages of the invention will become apparent from the following detailed description which is drafted with reference to the accompanying drawings.

BRIEF DESCRIPTIONS OF THE DRAWINGS

DETAILED DESCRIPTION OF THE PREFERRED EMBODIMENT

Figure 1:
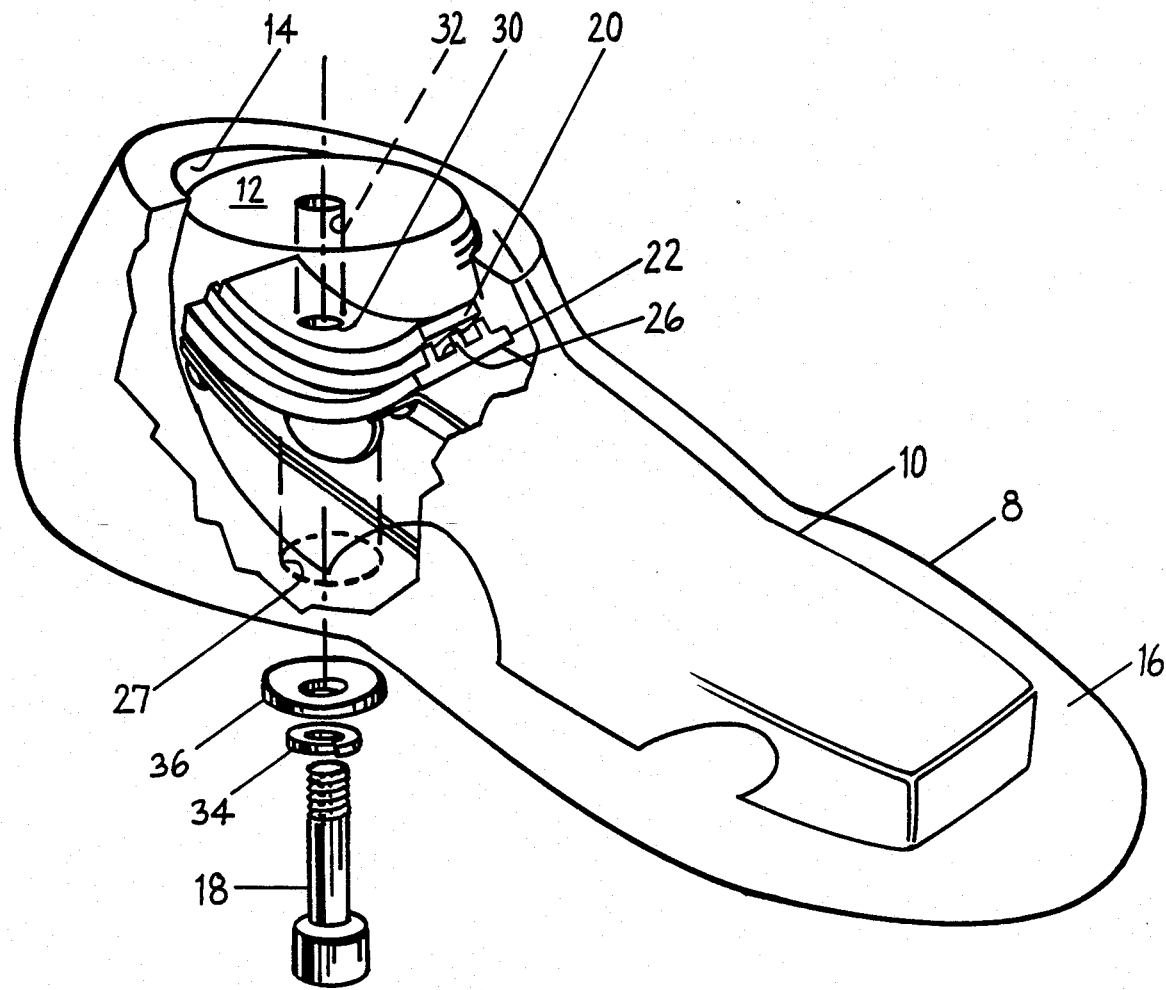
FIG. 1 is a partially broken perspective view of a foot incorporating the invention.
Figure 2:
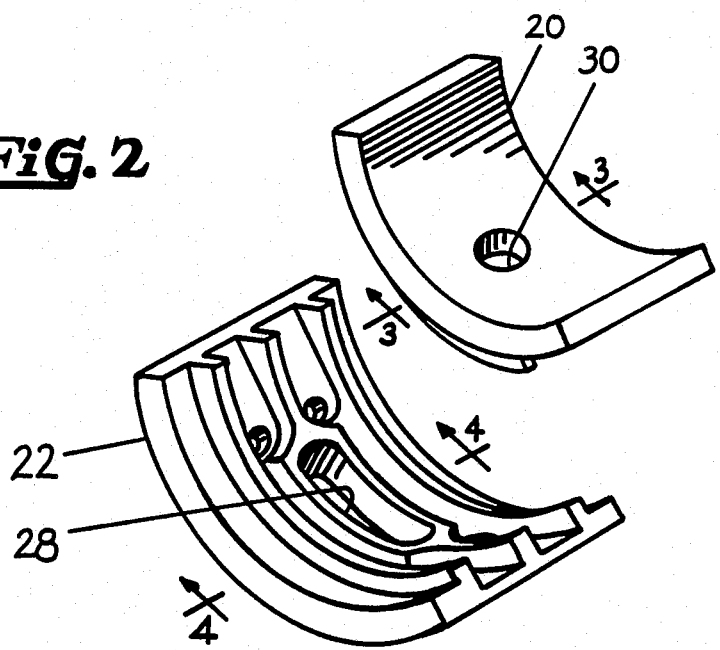
FIG. 2 is a perspective view of the adjustable locking mechanism of the invention.

Referring to the drawings a prosthetic foot incorporating the invention is indicated generally at 8. The foot includes an elongated one-piece semi-rigid keel 10, a bolt block 12, deposited within keel cavity 14 and an outer layer of rubber-like covering material 16 enveloping the entire foot.

Figure 5:
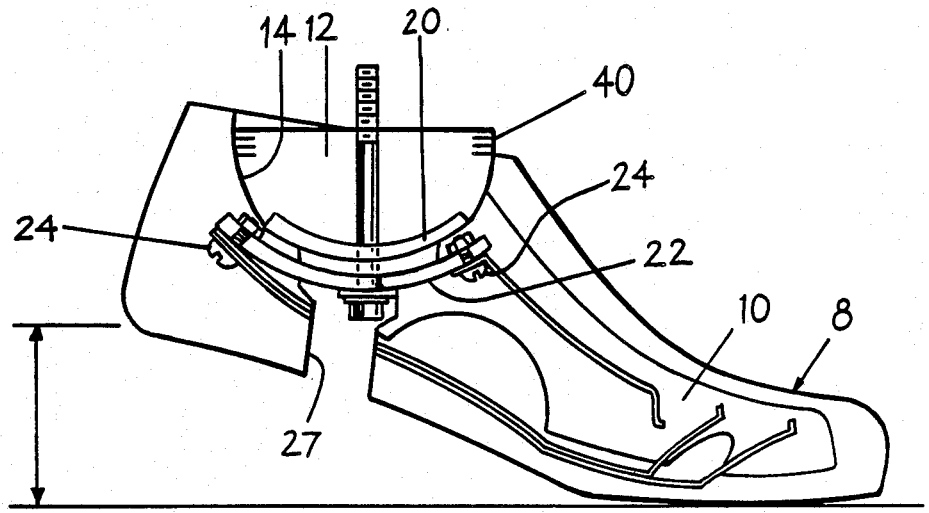
FIG. 5 is a sectional side elevational view of a foot adjusted for standard heel height.
Figure 6:
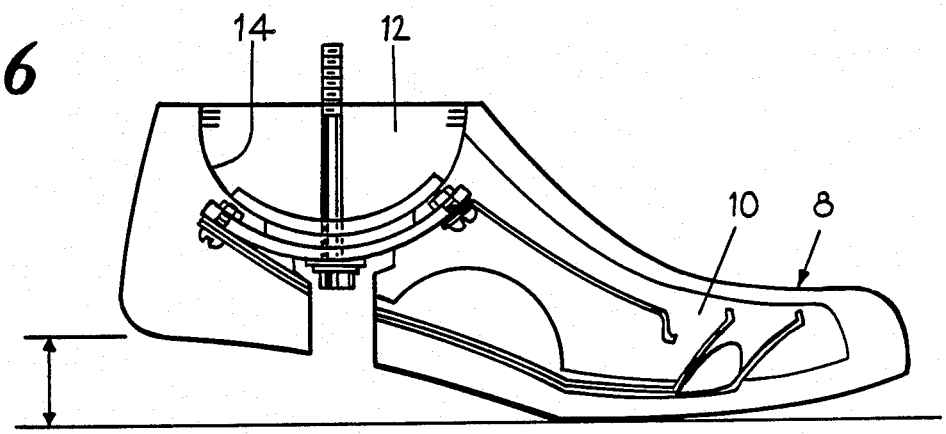
FIG. 6 is a sectional side elevational view of a foot adjusted for high heel position.
Figure 7:
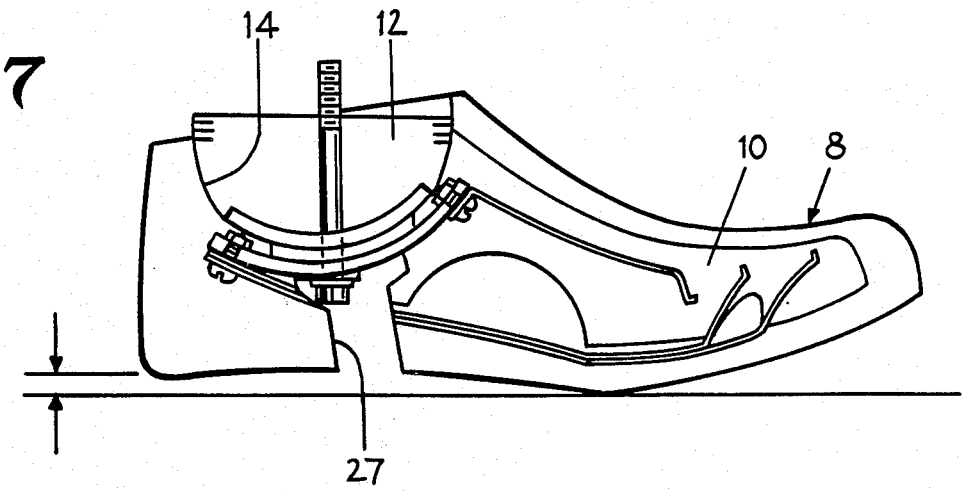
FIG. 7 is a sectional side elevational view of a foot adjusted for low heel position.

As seen in the longitudinal sectional views of FIGS. 5, 6 and 7 the block receiving cavity 14 in the keel 10 is arcuate in a direction longitudinally of the foot. The bolt block 12 received in the cavity 14 is provided with a lower surface that is arcuate in the same manner as the curve in cavity 14. Arcuate rail member 20 is permanently secured to the undersurface of bolt block 12 in any suitable manner such as, for example, by cementing. Arcuate track and groove member 22 is permanently secured to the curved surface of cavity 14 just below the rail member 20. The arcuate groove member 22 is permanently secured to the arcuate surface of the cavity 14 of the keel 10. Screws 24, 24 may be utilized for this purpose though any securing mode is satisfactory.

It will be understood that the rail member 20 and track or groove member 22 are identically curved. Furthermore, the rails 25, 25 of the member 20 are congruently deposited within the arcuate groove 26 of the number 22 assembly. As earlier noted the rails 24 and the grooves 26 are slightly wedge shaped as seen in transverse section and have a common arcuate pitch line so that they fit each other with locking type taper.

The foot 8 is provided with a lower access opening 27 which extends upwardly through the keel 10 and communicates with slot 28 in member 22. The slot 28 communicates with hole 30 in member 20 which in turn is aligned with opening 32 in bolt block 12.

The bolt 18, lock washer 34 and force distributing washer 36 are position in opening 27 so that the washer 36 is positioned to engage the lower surface of member 22. The threaded end of the bolt 18 extends upwardly through slot 28 hole 30 and opening 32 to conventionally and threadably engage the lower end of a prosthetic device (not shown) worn by the amputee. Upon tightening the bolt 18, rails 25, 25 are fixedly wedged within the grooves 26, 26 to firmly and positively hold the bolt block 12 in fixed position within cavity 14.

Figure 3:
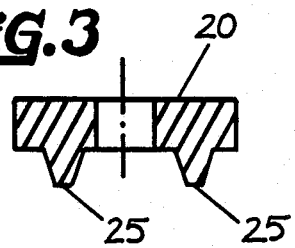
FIG. 3 is a sectional view taken along line 3—3 of FIG. 2.
Figure 4:
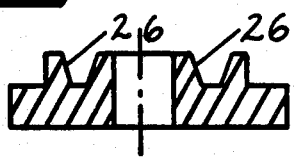
FIG. 4 is a sectional view taken along line 4—4 of FIG. 2.

In adjusting operation, it is suggested that the amputee initially set bolt block 12 at a standard position as shown in FIG. 5. The amputee then puts the prosthetic foot into his shoe and is observed walking by an assistant. A determination is made as to whether an adjustment of the heel height would improve the gait of the amputee. The heel height is then raised or lowered as illustrated in FIG. 3 or FIG. 4 experimentally until the optimum walking gait of the amputee is acheived. Similar experimental adjustment is made with all the shoes the amputee desires to wear and, selected marks 40 may be placed on bolt block 12 to indicate the proper angular relation of the bolt block 12 within the cavity 14 for each particular shoe. Thereafter it is only necessary for the amputee to properly locate the bolt block 12 within the cavity 14 for the particular shoe he intends to wear.

With the above description of the presently preferred embodiment it should be apparent to those skilled in the art that the features of the disclosed invention are subject to modification in arrangement and detail all within the spirit and scope of the invention.

What is claimed is:

1. In a heel height adjusting arrangement for a prosthetic foot, the combination of a prosthetic foot having a cavity at the rear end of the foot, a bolt block disposed in the cavity, interfitting means for varying the physical position of the bolt block in the cavity whereby the heel height of the prosthetic foot may be varied by the wearer of the foot, and said interfitting means including means for locking the bolt block within the cavity in a determined fixed position when the foot is in use, said locking means comprising interfitting rails and grooves on the prosthetic foot and bolt block respectively, to provide locking engagement between the bolt block and the foot.

2. A heel height adjusting arrangement for a prosthetic foot according to claim number 1, wherein interfitting rails and grooves are arcuate as seen in side elevation.

3. In an arrangement for adjusting the heel height of a prosthetic foot, the combination of a prosthetic foot having an upwardly facing cavity at the rear aspect of the foot, the upwardly facing surface of said cavity being arcuate in form longitudinally of the foot and as seen in side elevational view, a securing block disposed in the cavity and having a lower arcuate surface arranged to complement the arc formed in the cavity and member means on the respective arcuate surfaces for lockably and variably connecting said securing block to the prosthetic foot and in selectable predetermined relationships between the block the foot.

4. An arrangement for adjusting the heel height of a prosthetic foot according to claim number 4, wherein the member means comprises arcuate grooves on one of said surfaces complementary receiving arcuate rails on the other said surfaces.

* * * * *